(12) United States Patent
Satou et al.

(10) Patent No.: US 7,914,457 B2
(45) Date of Patent: Mar. 29, 2011

(54) ULTRASONIC PROBE OF RADIAL SCAN TYPE, ULTRASONIC OBSERVATION APPARATUS AND ULTRASONIC DIAGNOSING SYSTEM

(75) Inventors: Yoshiaki Satou, Kanagawa (JP); Tomoo Sato, Kanagawa (JP); Hiroyuki Karasawa, Kanagawa (JP); Kazuhiro Tsujita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1574 days.

(21) Appl. No.: 11/244,297

(22) Filed: Oct. 6, 2005

(65) Prior Publication Data

US 2006/0074317 A1    Apr. 6, 2006

(30) Foreign Application Priority Data

Oct. 6, 2004    (JP) ................ 2004-293619

(51) Int. Cl.
*A61B 8/14* (2006.01)
*A61B 8/00* (2006.01)
*G01N 9/24* (2006.01)

(52) U.S. Cl. ........... 600/459; 600/437; 600/443; 73/626
(58) Field of Classification Search .......... 600/437, 600/462–463, 443, 440, 459, 444–445, 447; 370/360, 535, 546, 916; 73/625–626
See application file for complete search history.

(56) References Cited

U.S. PATENT DOCUMENTS

| | | | |
|---|---|---|---|
| 5,081,993 A | 1/1992 | Kitney et al. | |
| 5,279,301 A * | 1/1994 | Tsukaya et al. | 600/442 |
| 5,902,244 A * | 5/1999 | Kobayashi et al. | 600/447 |
| 5,924,993 A * | 7/1999 | Hadjicostis et al. | 600/462 |
| 6,174,286 B1 | 1/2001 | Ramamurthy et al. | |
| 2005/0126292 A1 | 6/2005 | Amemiya | |

FOREIGN PATENT DOCUMENTS

| | | |
|---|---|---|
| JP | 02-134142 A | 5/1990 |
| JP | 2004 174227 | 6/2004 |

OTHER PUBLICATIONS

European Search Report for Application No. 05021678.7—2305 dated Dec. 23, 2005.

* cited by examiner

*Primary Examiner* — Long V Le
*Assistant Examiner* — Katherine L Fernandez
(74) *Attorney, Agent, or Firm* — Sughrue Mion, PLLC

(57) ABSTRACT

An ultrasonic probe of a radial scan type mountable on an ultrasonic observation apparatus, which inputs and outputs M numbers of signals in parallel, comprises the following: N (N>M) numbers of ultrasonic transducers disposed on an outer periphery of a tip, and grouped into plural sensor element groups activated in sequence, each of which has M numbers of ultrasonic transducers; N numbers of first signal lines respectively connected to the N numbers of ultrasonic transducers for transmitting a drive signal for driving the ultrasonic transducers and an echo signal from within a living organism; M numbers of second signal lines connected to the ultrasonic observation apparatus; and a multiplexer disposed between the first signal lines and the second signal lines, which selectively switches M numbers of the first signal lines for respectively connecting to the second signal lines according to the sensor element group to be activated.

32 Claims, 9 Drawing Sheets

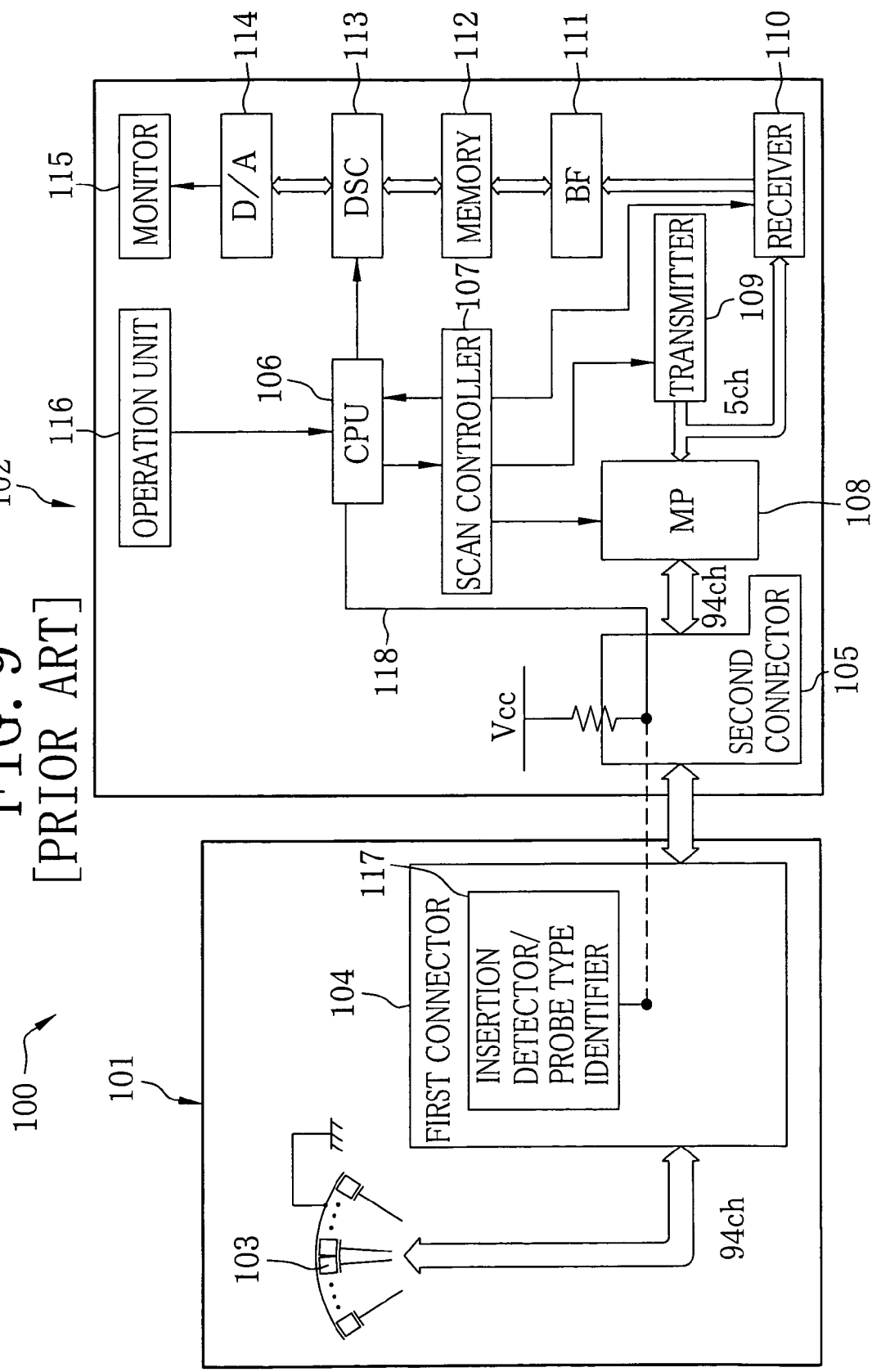
FIG. 9 [PRIOR ART]

ULTRASONIC PROBE OF RADIAL SCAN TYPE, ULTRASONIC OBSERVATION APPARATUS AND ULTRASONIC DIAGNOSING SYSTEM

BACKGROUND OF THE INVENTION

1. Field of the Invention

The present invention relates to an ultrasonic probe of a radial scan type which is compatible with an ultrasonic probe of a convex scan type, an ultrasonic observation apparatus which is capable of connecting the ultrasonic probes of the radial scan type and the convex scan type, and an ultrasonic diagnosing system.

2. Background Arts

Recently, in a field of medical care, a medical diagnosis using ultrasonic images is widely used. In an ultrasonic diagnosis, an ultrasonic is emitted to a required area of a living organism from an ultrasonic probe, and an echo reflected from within the living organism is received and converted into an electronic signal. The echo signal is analyzed and converted into an image. Further, an ultrasonic probe of an electronic scan type is also known, which is provided with plural ultrasonic transducers for transmitting and receiving the ultrasound. The ultrasonic probe of the electronic scan type selectively drives the ultrasonic transducers by using an electronic switch or the like.

As the ultrasonic probe of the electronic scan type, there are a convex scan type and a radial scan type (see Japanese Patent Laid-Open Publication No. 2-134142). The ultrasonic probe of the convex scan type has, plural (for instance, 94 to 128) ultrasonic transducers disposed in a sector shape on a tip of the probe. The ultrasonic probe of the radial scan type has a plurality of (for instance, 360) ultrasonic transducers all around an outer periphery of a tip of the probe.

FIG. 9 shows a conventional ultrasonic diagnosing system 100 of a convex scan type. The ultrasonic diagnosing system 100 is constructed of an ultrasonic probe 101 and an ultrasonic observation apparatus 102 to which the ultrasonic probe 101 is connected. It is possible to design an ultrasonic observation apparatus of a radial scan type by using a structure of the ultrasonic observation apparatus of the convex scan type. However, since the ultrasonic transducers of the radial scan type has more number of ultrasonic transducers, it is necessary to increase the number of input/output lines in each circuit. For instance, terminals of a second connector 105, input lines of a multiplexer (MP) 108, control lines of a scan controller 107 and the like should be increased in number. Likewise, a beamformer (BF) 111 should be modified according to the increase in the number of sound rays forming the ultrasonic image. In the modification, it becomes necessary to newly design the multiplexer 108, the scan controller 107 and the BF 111 in accordance with the number of the ultrasonic transducers, which result in a long-term development and an increasing cost.

Further, an ultrasonic observation apparatus, which is capable of applying both the ultrasonic probes of the convex scan type and the radial scan type, is desired. In particular, it is preferable that the ultrasonic observation apparatus of the convex scan type can be easily modified so as to connect the ultrasonic probe of the radial scan type.

SUMMARY OF THE INVENTION

A main object of the present invention is to provide a compatible ultrasonic observation apparatus which is capable of connecting ultrasonic probes of a convex scan type and a radial scan type.

Another object of the present invention is to provide a compatible ultrasonic observation apparatus and an ultrasonic diagnosing system, which can be easily manufactured at a low cost, by utilizing a structure of the ultrasonic observation apparatus of the convex scan type.

Further another object of the present invention is to provide a compatible ultrasonic observation apparatus which is manufactured by modifying the ultrasonic observation apparatus of the convex scan type with ease at low cost.

Further another object of the present invention is to provide an ultrasonic probe of a radial scan type which is compatible with the ultrasonic probe of the convex scan type.

In order to achieve the above and other objects, the ultrasonic probe of the radial scan type according to the present invention includes a multiplexer disposed between N numbers of first signal lines and M (N>M) numbers of second signal lines. On an outer periphery of a tip of the ultrasonic probe, N numbers of ultrasonic transducers are disposed. The ultrasonic transducers are respectively connected to the first signal lines. The first signal line transmit a drive signal for driving the ultrasonic transducer, and an echo signal from within a living organism. The second signal lines are connected to the ultrasonic observation apparatus which inputs and outputs M numbers of signals in parallel through a connector section thereof. To the ultrasonic observation apparatus, the ultrasonic probe of the convex scan type, which has M numbers of ultrasonic transducers on an outer periphery of a tip of the probe, can be connected in addition to the ultrasonic probe of the radial scan type. The multiplexer selects M numbers of ultrasonic transducers included in one of sensor element groups among N numbers of ultrasonic transducers to connect to the ultrasonic observation apparatus.

N numbers of ultrasonic transducers are disposed throughout the outer periphery at a predetermined pitch. N numbers of ultrasonic transducers are grouped into four sensor element groups. The plural ultrasonic transducers disposed at a boundary of two adjacent sensor element groups are contained in the two adjacent sensor element groups. It is preferable that the ultrasonic transducer is provided in an endoscope.

The ultrasonic observation apparatus of the present invention includes a connector section for inputting and outputting M numbers of signals in parallel, a type identifier, and a scan controller. The type identifier identifies a type of the ultrasonic probe mounted through the connector section thereof. The scan controller selects one of a first mode and a second mode according to the type identification of the type identifier. The first mode is applied to the ultrasonic probe of the radial scan type, and the second mode is applied to the ultrasonic probe of the convex scan type. In the first mode, a control signal is output for a switching operation of a multiplexer incorporated in the ultrasonic probe of the radial scan type. In the second mode, the control signal is not output.

The ultrasonic diagnosing system of the present invention includes the ultrasonic probe of the radial scan type and the ultrasonic observation apparatus on which the ultrasonic probe of the radial scan type is mounted through the connecter. The ultrasonic probe of the radial scan type includes the N numbers of ultrasonic transducers disposed on the outer periphery of the tip of the probe, the N numbers of first signal lines respectively connected to the N numbers of ultrasonic transducers, M numbers of second signal lines and a multiplexer disposed between the first signal lines and the second signal lines. The multiplexer selectively switches M numbers of first signal lines to connect to the second signal lines. The ultrasonic observation apparatus includes the connector section for inputting and outputting M numbers of signals in parallel and a scan controller. The scan controller performs the switching operation of the multiplexer incorporated in the ultrasonic probe of the radial scan type. The ultrasonic observation apparatus further includes the type identifier which identifies a type of an ultrasonic probe mounted on the connector. The scan controller selects the first mode for the ultrasonic probe of the radial scan type, and the second mode for the ultrasonic probe of the convex scan type according to the type identification of the type identifier. In the first mode, the multiplexer performs the switching operation. In the second mode, the switching operation is not performed.

In a preferable embodiment, the ultrasonic observation apparatus of the present invention includes the connector section, a first multiplexer and a second multiplexer. The first signal lines, which are connected to the ultrasonic transducers, are connectable to the connector section. The first multiplexer selectively switches M numbers of first signal lines and connect to the M numbers of second signal lines. The second multiplexer selectively switches L (N>M>L) numbers of second signal lines to connect to a transmitter, which transmits the drive signal, or a receiver which receives the echo signal.

In a preferable embodiment of the present invention, the ultrasonic diagnosing system includes the ultrasonic probe of the radial scan type in which N numbers of ultrasonic transducers are disposed on the outer periphery of the tip of the probe, and the ultrasonic observation apparatus on which the ultrasonic probe of the radial scan type is mounted through the connector section. L numbers of ultrasonic transducers are simultaneously driven as one block. At least one of ultrasonic transducers is shifted every time the drive signal for driving the ultrasonic transducer is transmitted or the echo signal is received from the living organism. An ultrasonic image is generated from the echo signal sequentially received on the block basis. The ultrasonic observation apparatus includes the first multiplexer, the second multiplexer and the scan controller. The first multiplexer selectively switches M (N>M>L) numbers of first signal lines to connect to the M numbers of second signal lines. The second multiplexer selectively switches L numbers of second signal lines to connect to the transmitter for transmitting the drive signal or the receiver for receiving the echo signal. The scan controller controls the switching operation of the first and second multiplexers.

In a further preferable embodiment of the present invention, the ultrasonic observation apparatus includes the connector section, on which the ultrasonic probe is mounted, and the multiplexer. The N numbers of first signal lines, which are respectively connected to the ultrasonic transducers, are connectable to the connector section. A multiplexer selectively switches L (N>L) numbers of first signal lines for connecting to L numbers of second signal lines. The second signal lines are connected to the transmitter for transmitting the drive signal and the receiver for receiving the echo signal. It is preferable to use a programmable logic circuit, in which an arbitrary logic is reprogrammable, as the multiplexer.

In a further preferable embodiment of the ultrasonic diagnosing system of the present invention, the ultrasonic probe of the radial scan type includes the first multiplexer which selectively switches M numbers of first signal lines to connect to the second signal lines. The ultrasonic observation apparatus includes the second multiplexer and the scan controller. The second multiplexer selectively switches L numbers of second signal lines to connect to the transmitter for transmitting the drive signal or the receiver for receiving the echo signal.

In a still further preferable embodiment of the present invention, the ultrasonic diagnosing system includes the multiplexer disposed in one of the ultrasonic probe of the radial scan type or the ultrasonic observation apparatus. The multiplexer selects M numbers of signal lines out of the N numbers of signal lines.

Since the ultrasonic probe of the radial scan type uses the same number of output lines as the ultrasonic probe of the convex scan type by the function of the multiplexer, the ultrasonic probe of the radial scan type has become compatible with the ultrasonic probe of the convex scan type. Further, the ultrasonic probe of the radial scan type can be manufactured at low cost by only incorporating the multiplexer.

Since the ultrasonic observation apparatus of the present invention has a function to switch the multiplexer when the ultrasonic probe of the radial scan type incorporated with the multiplexer is connected, so that both the ultrasonic probes of the radial scan type and the convex scan type can be applied. Further, since the ultrasonic observation apparatus of the present invention utilizes the fundamental structure of the ultrasonic observation apparatus of the convex scan type, the manufacturing or the modification thereof can be performed at low cost.

Since the ultrasonic observation apparatus of the preferable embodiment has at least one multiplexer and divides the signals from the ultrasonic probe of the radial scan type, the configuration of the conventional ultrasonic observation apparatus of the convex scan type can be utilized. Accordingly, the ultrasonic observation apparatus can be easily designed and manufactured at low cost.

BRIEF DESCRIPTION OF THE DRAWINGS

The above objects and advantages of the present invention will become apparent from the following detailed descriptions of the preferred embodiments when read in association with the accompanying drawings, which are given by way of illustration only and thus do not limit the present invention. In the drawings, the same reference numerals designate like or corresponding parts throughout the several views, and wherein:

FIG. 9 is a schematic view showing a conventional ultrasonic diagnosing system.

DETAILED DESCRIPTION OF THE EMBODIMENTS

Figure 1:
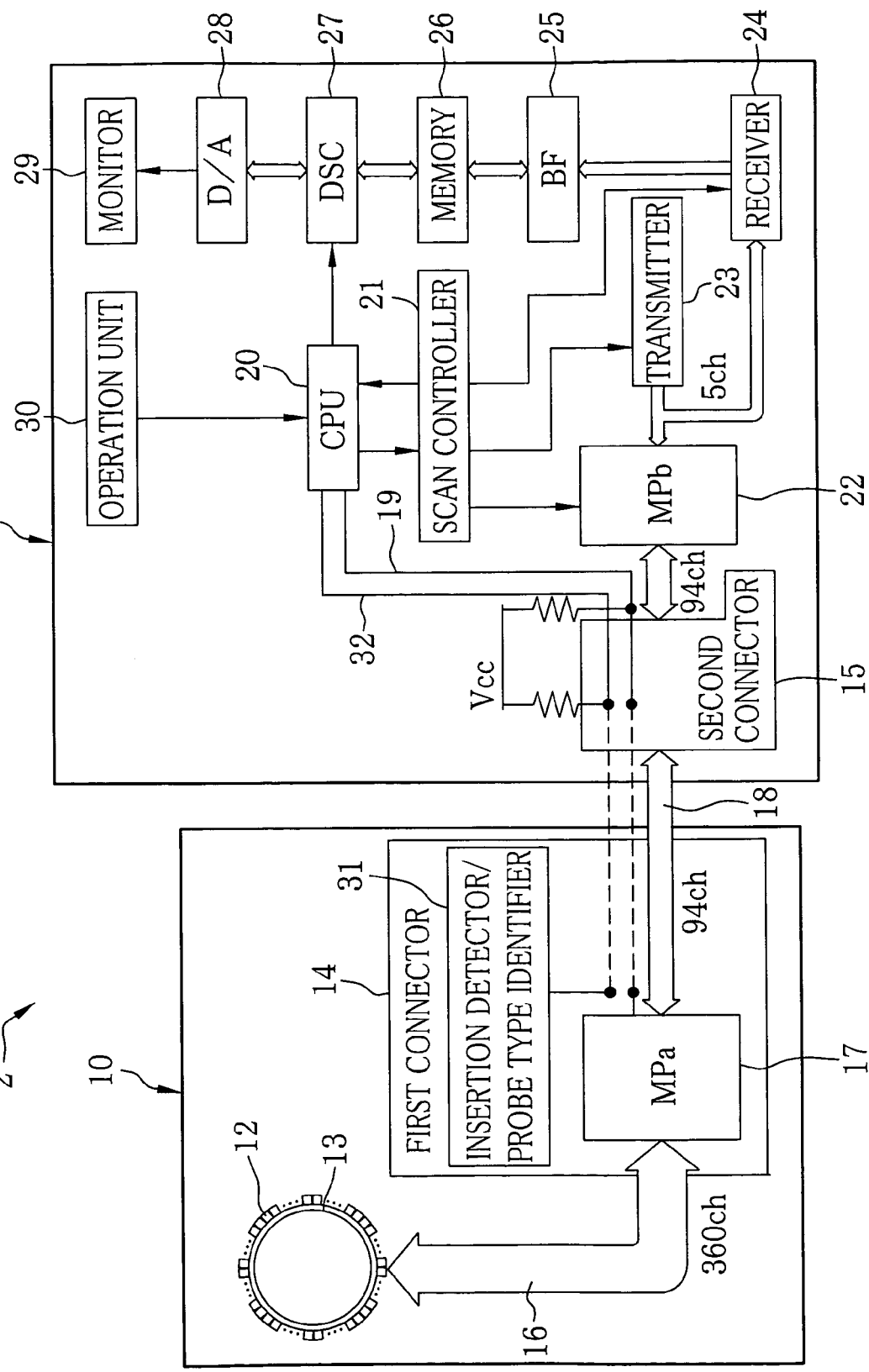
FIG. 1 is a schematic view showing a first embodiment of an ultrasonic diagnosing system.

In FIG. 1, an ultrasonic diagnosing system 2 as a first embodiment of the present invention is constructed of an ultrasonic probe 10 and an ultrasonic observation apparatus 11. The ultrasonic probe 10 is of a radial scan type which is incorporated with a cylindrical substrate 13 with 360 ultrasonic transducers 12 disposed at regular intervals on an outer periphery on a tip of a sheath (not shown) formed of a flexible member. The ultrasonic probe 10 is connected to the ultrasonic observation apparatus 11 by inserting a first connector 14, which is provided at a trailing end of a code (not shown) extended from the sheath, into a second connector 15 provided in the ultrasonic observation apparatus 11.

The 360 ultrasonic transducers 12 are respectively connected to ends of 360 first signal lines 16 which transmit drive signals from a transmitter 23 (which will be described later) of the ultrasonic observation apparatus 11 and echo signals reflected from within a living organism. The other ends of the first signal lines 16 are respectively connected to a multiplexer (MPa) 17.

Figure 2:
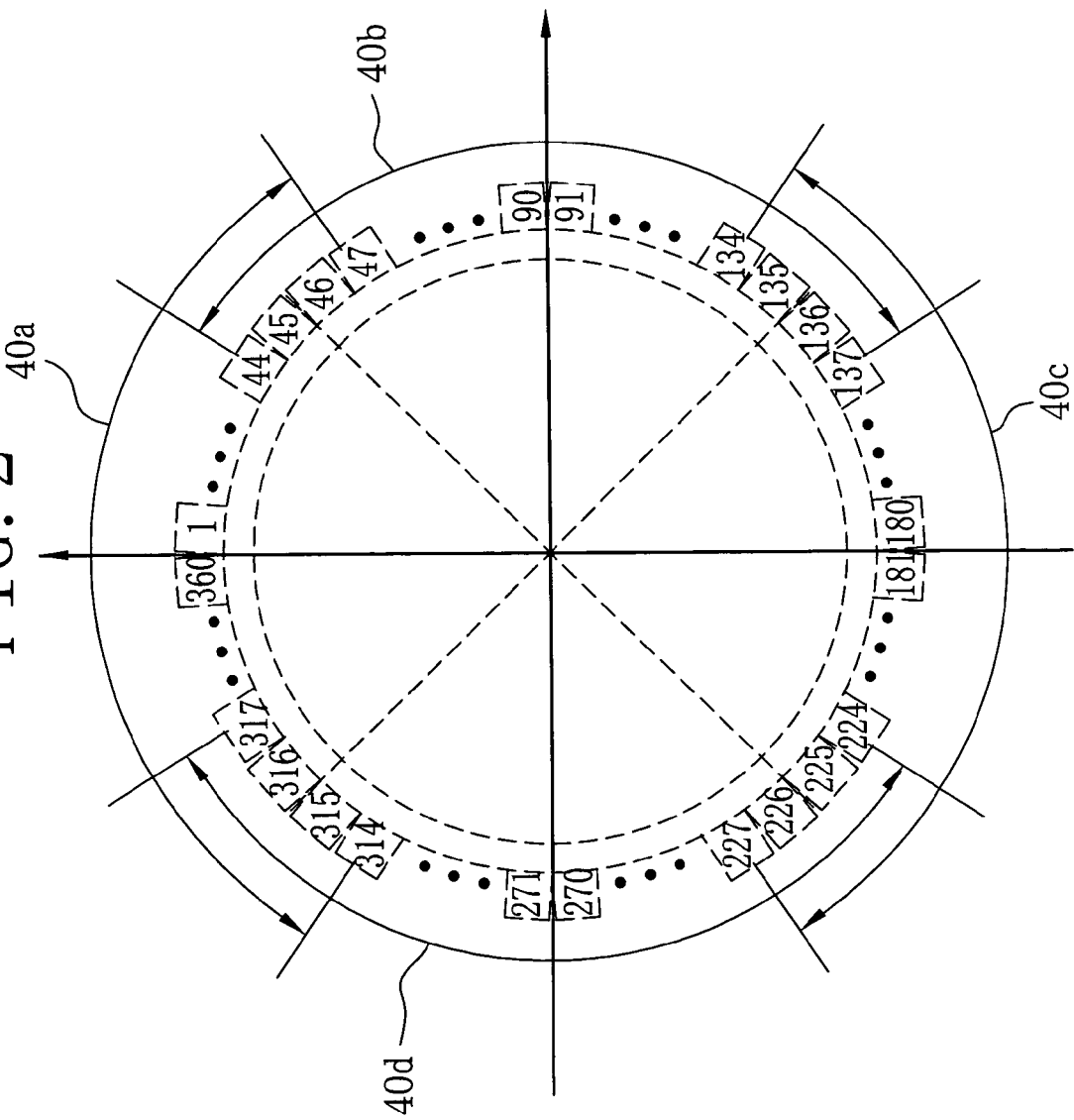
FIG. 2 is an explanatory view showing a method for dividing ultrasonic transducers into plural sensor element groups.

As shown in FIG. 2, the 360 ultrasonic transducers 12 are divided into four sensor element groups 40a (a first sensor element group which includes the ultrasonic transducers Nos. 1-47 and 314-360), 40b (a second sensor element group which includes the ultrasonic transducers Nos. 44-137), 40c (a third sensor element group which includes the ultrasonic transducers Nos. 134-227) and 40d (a fourth sensor element group which includes the ultrasonic transducers Nos. 224-317). The four sensor element groups 40a-40d divide the outer periphery of the cylindrical substrate 13 into four approximately equal portions.

There are 94 ultrasonic transducers 12 in each sensor element group. At the boundary of the first sensor element group 40a and the second sensor element group 40b, the ultrasonic transducers 12 Nos. 44-47 are contained in both element groups. At the boundary of the second sensor element group 40b and the third sensor element group 40c, the ultrasonic transducers Nos. 134-137 are contained in both sensor element groups. At the boundary of the third sensor element group 40c and the fourth sensor element group 40d, the ultrasonic transducers Nos. 224-227 are contained in both element groups. At the boundary of the fourth sensor element group 40d and the first sensor element group 40a, the ultrasonic transducers Nos. 314-317 are contained in both element groups. Note that Nos. 1-360 are the numbers assigned to each of the ultrasonic transducers in a clockwise direction for the sake of convenience.

In FIG. 1, a control line 19 is connected to the MPa 17. The control line 19 receives an element group selection signal from a CPU 20 (which will be described later) of the ultrasonic observation apparatus 11. According to the sensor element group selection signal, the MPa 17 switches the signal of 360 channels, which is transmitted from the first to fourth sensor element groups 40a-40d through the first signal lines 16, to that of 94 channels in the selected sensor element group. One end of each of 94 second signal lines 18 is connected to the MPa 17. The other end of each of the 94 second signal lines 18 is connected to the ultrasonic observation apparatus 11 through the second connector 15.

Figure 3:
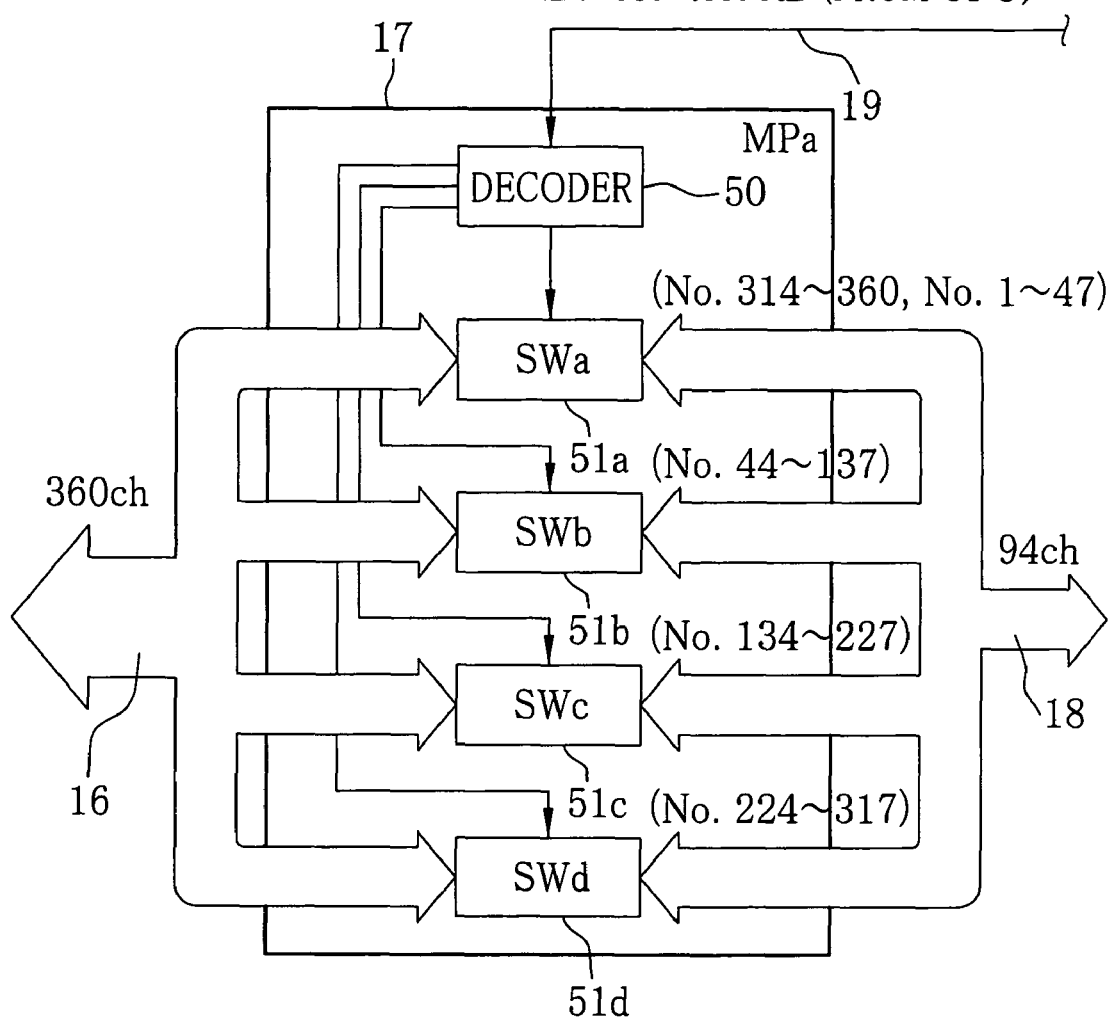
FIG. 3 is a schematic view showing a multiplexer.

As shown in FIG. 3, the MPa 17 is constructed of a decoder 50, and first to fourth switches (SWa-SWd) 51a-51d which are constituted of FET and the like. The decoder 50 receives and decodes the sensor element group selection signal of two-bit sent from the CPU 20 of the ultrasonic observation apparatus 11 through the control line 19.

The signals from the ultrasonic transducers 12 of the first to fourth sensor element groups 40a-40d are respectively input to the corresponding switches (SWa-SWd) 51a-51d through the first signal lines 16. The overlapping transducers 12 at the boundaries between the first to the fourth sensor element groups 40a-40d are connected to each of the corresponding switches (SWa-SWd) 51a-51d.

The first to the fourth switches (SWa-SWd) 51a-51d are switched between on and off according to the sensor element group selection signals decoded in the decoder 50. To be more specific, for instance, when the sensor element group selection signal is "00", the first sensor element group 40a is selected. At that time, the SWa 51a is turned on while the SWb-SWd 51b-51d are turned off. When the sensor element group selection signal is "01", the second sensor element group 40b is selected. At that time, the SWb 51b is turned on while the SWa 51a, SWc 51c and SWd 51d are turned off. Further, when the sensor element group selection signal is "10", the third sensor element group 40c is selected. At that time, the SWc 51c is turned on while the SWa 51a, SWb 51b and SWd 51d are turned off. When the sensor element group selection signal is "11", the fourth sensor element group 40d is selected. At that time, the SWd 51d is turned on while the SWa-SWc 51a-51c are turned off.

In FIG. 1, the ultrasonic observation apparatus 11 is thoroughly controlled by the CPU 20. A scan controller 21 is connected to the CPU 20. The scan controller 21 is connected to a multiplexer (MPb) 22, the transmitter 23 and a receiver 24, and transmits a reference pulse to each of the above sections to control the operation. An ultrasonic probe of a convex scan type with 94 channels has 94 ultrasonic transducers disposed in a sector shape on its tip (not shown). In a connector section of the ultrasonic probe of the convex scan type, an insertion detector/probe type identifier, which has the same function as an insertion detector/probe type identifier 31, is provided, which will be described later.

The MPb 22 selectively switches the signals of five channels out of 94 channels which are input and output through the second connector section 15. The drive signal of five channels is input from the transmitter 23 to the MPb 22, and the MPb 22 outputs the echo signal of five channels to the receiver 24.

The MPb 22 simultaneously drives the five selected ultrasonic transducers 12 as one block, out of one of the sensor element group selected by the MPa 17, under the control of the scan controller 21. Further, as shown in FIG. 2, the MPb 22 selectively switches the ultrasonic transducer 12, which receives and transmits the drive signal and the echo signal, by shifting at least one ultrasonic transducer 12 to be driven in the clockwise direction every time the drive signal and the echo signal are transmitted and received.

Under the control of the scan controller 21, the transmitter 23 transmits the drive signal (a voltage pulse with five channels for driving the ultrasonic transducer 12) to the ultrasonic transducer 12 selected by the MPb 22.

Under the control of the scan controller 21, the receiver 24 receives the echo signal (five channels) reflected from within the living organism, which is obtained by the ultrasonic transducers 12 selected by the MPb 22, and performs Sensitivity Time Control (STC) process to the received echo signal. In the STC, the sensitivity is adjusted according to the time which corresponds to a propagation distance (depth) of the ultrasound. The respective timings of the transmission and the reception of the transmitter 23 and the receiver 24 are switched by the scan controller 21.

The echo signal received by the receiver 24 is input to a beamformer (BF) 25. The echo signal of five channels is delayed by the BF 25 for a predetermined time to be co-phased, and added.

The echo signal, which is added in the BF 25, is digitalized and then stored in a memory 26. A digital scan converter (DSC) 27 reads the digital signal from the memory 26 under the control of the CPU 20, and converts the read digital signal into a television signal of a NTSC format. A D/A converter 28 converts the signal, which has been converted into the NTSC format by the DSC 27, into the analog signal again. A monitor 29 displays the analog signal converted by the D/A converter 28 as an ultrasonic image.

In addition to the above mentioned scan controller 21 and the DSC 27, an operation unit 30 and a serial signal line 32, through which a notification signal from the insertion detector/probe type identifier 31 provided in the first connector 14 of the ultrasonic probe 12 is transmitted, are connected to the CPU 20. The operation unit 30 is constructed of an operation panel in which various operation buttons are disposed, for instance. The CPU 20 controls the operation of each section according to the signals input from the operation unit 30.

An identification code, which indicates that the ultrasonic probe 12 is of the radial scan type, is stored in the insertion detector/probe type identifier 31. The insertion detector/probe type identifier 31 transmits the identification code to the CPU 20 by a serial communication through the serial signal line 32. Further, the CPU 20 detects the insertion of the ultrasonic probe by receiving the identification code.

When the CPU 20 receives the insertion detection signal and the identification signal from the insertion detector/probe type identifier 31, and identifies that the ultrasonic probe of the convex scan type with the 94 channels is connected, the CPU 20 controls the operation of the MPb 22 through the scan controller 21 without transmitting the sensor element group selection signal to the MPa 17 (a first mode). When the CPU 20 identifies that the ultrasonic probe 10 of the radial scan type with the 360 channels is connected, the CPU 20 transmits the sensor element group selection signal to MPa 17 through the control line 19 and controls the operation of the MPb 22 through the scan controller 21 (a second mode).

Figure 4:
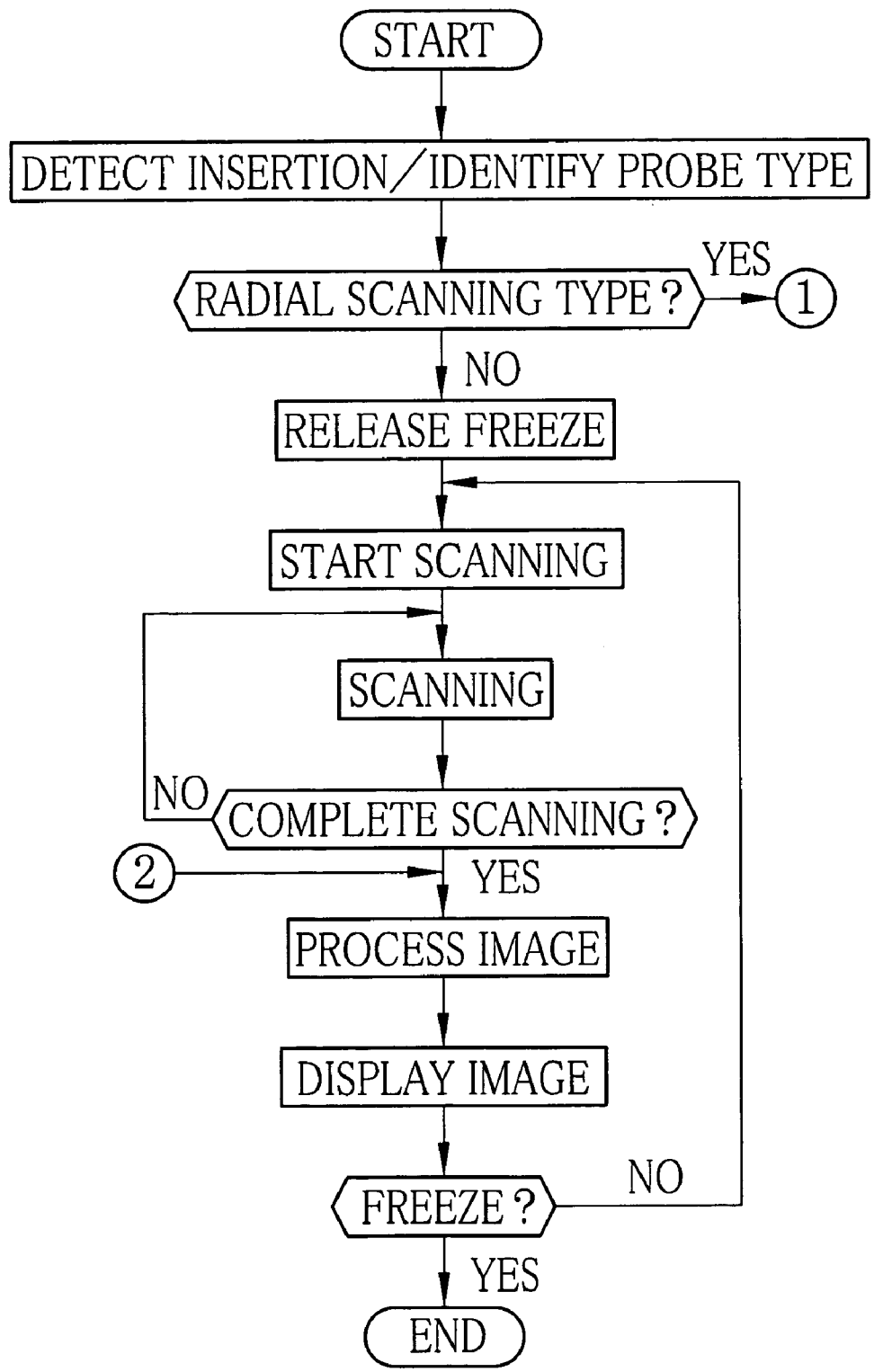
FIG. 4 is a flow chart showing operational steps of the ultrasonic diagnosing system when an ultrasonic probe of a convex scan type is connected.

Next, the operation of the ultrasonic diagnosing system 2 of the above configuration is described with reference to flowcharts in FIGS. 4 and 5. In FIG. 4, when the CPU 20 identifies that the ultrasonic probe of the convex scan type with the 94 channels is connected to the ultrasonic observation apparatus 11, the freeze is released by operating the operation unit 30. Thereafter, the drive signal of five channels is transmitted from the transmitter 23 under the control of the scan controller 21.

The drive signal is transmitted from the transmitter 23 to the desired block of the ultrasonic transducers selected by the MPb 22, through the first and second connectors 14 and 15. The ultrasonic transducers are driven by the drive signal so that the ultrasound is emitted to the living organism.

After the drive signal has been transmitted, the scan controller 21 switches from the transmission of the transmitter 23 to the reception of the receiver 24. Thereby, the echo signal reflected from within the living organism, which is obtained by the ultrasonic transducers, is input to the receiver 24 through the first and second connectors 14, 15 and the MPb 22.

The receiver 24 performs the STC (Sensitivity Time Control) process to the input echo signal. Then, the echo signal is added by the BF 25, and digitalized. The digital signal is stored in the memory 26. Thereafter, the above process is repeated through the last block while the MPb 22 shifts the ultrasonic transducer, which is to be driven, one by one under the control of the scan controller 21.

When the scanning by the 94 ultrasonic transducers is completed, the DSC 27 reads the digital echo signal stored in the memory 26 and converts into the NTSC format. The signal converted into the NTSC format is re-converted into the analog signal by the D/A converter 28 and displayed as the ultrasonic image on the monitor 29. The above sequential process is continued until the operation unit 30 is operated to issue a command to freeze.

Figure 5:
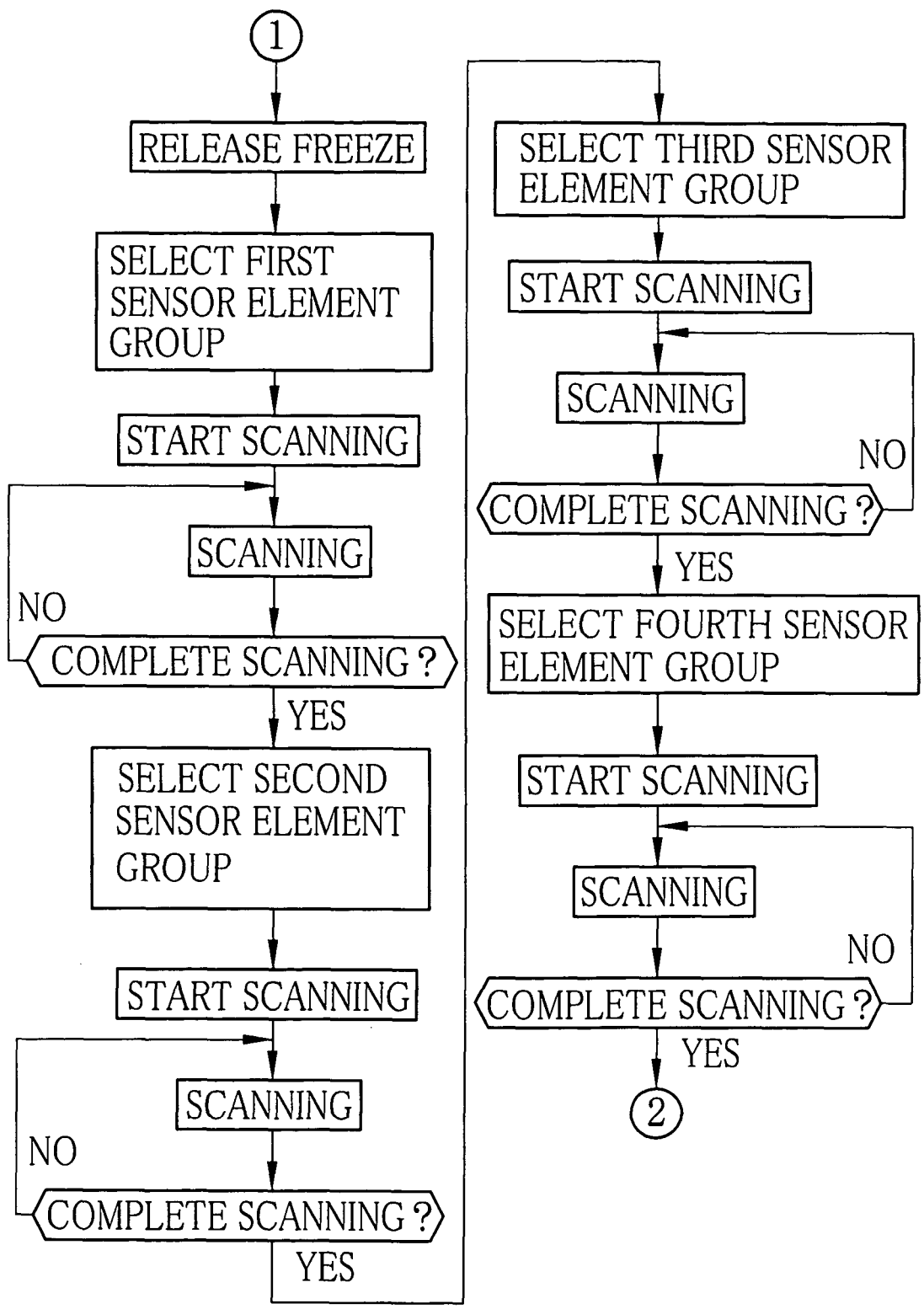
FIG. 5 is a flow chart showing the operational steps of the ultrasonic diagnosing system when an ultrasonic probe of a radial scan type is connected.

When the CPU 20 identifies that the ultrasonic probe 12 of the radial scan type with the 360 channels is connected to the ultrasonic observation apparatus 11, as shown in FIG. 5, after the freeze is released by operating the operation unit 30, the transmitter 23 transmits the drive signal of five channels under the control of the scan controller 21.

The drive signal from the transmitter 23 is transmitted to the desired block of the ultrasonic transducers 12 selected by the MPb 22 from one of the sensor element groups 40a-40d selected by the MPa 17 according to the sensor element group selection signal sent from the CPU 20 through the control line 19. The ultrasonic transducer 12 is driven by the drive signal and thereby the ultrasound is emitted to the living organism.

After the drive signal has been transmitted, the scan controller 21 switches from the transmission of the transmitter 23 to the reception of the receiver 24. The echo signal reflected from within the living organism, which is obtained by the ultrasonic transducers, is input to the receiver 24 through the first and second connectors 14 and 15, and the MPb 22.

In the receiver 24, the STC process is performed to the input echo signal. Then, the signal is added by the BF 25, digitalized, and stored in the memory 26. Thereafter, under the control of the scan controller 21, the above process is repeated through the last block, while the MPb 22 shifts the ultrasonic transducer to be driven one by one.

In the MPa 17, the sensor element group selection signal transmitted from the CPU 20 is decoded by the decoder 50. The sensor element group selection signal "00" is sent to turn on the SWa 51a and turn off the SWb-SWd 51b-51d in the MPa 17. Thereby, the first sensor element group 40a is selected. In that state, the above process is performed through the last block of the first sensor element group 40a. Thereafter, the sensor element group selection signal "01" is transmitted to turn on the SWb 51b and turn off the SWa 51a, SWc 51c and SWd 51d in the MPa 17. Thereby, the second sensor element group 40b is selected and the above process is performed in the second sensor element group 40b. Thereafter, the sensor element group selection signal "10" and "11" are transmitted in this order so that the third and the fourth sensor element groups 40c and 40d are selected sequentially and the above process is respectively performed in the third and fourth sensor element groups 40c and 40d.

When the scanning by the 360 ultrasonic transducers 12 is completed, the digital echo signal stored in the memory 26 is read by the DSC 27 and converted into the NTSC format in the same manner as to when the ultrasonic transducer of the convex scan type is connected. Thereafter, the signal is reconverted into the analog signal in the D/A converter 28, and displayed on the monitor 29 as the ultrasonic image. The above process is repeated until the operation unit 30 is operated to issue the command to freeze.

As described above, since the 360 ultrasonic transducers are divided into four sensor element groups 40a-40d, and the MPa 17, which selectively connects the 94 first signal lines 16 out of the 360 first signal lines 16 to the second signal lines 18 according to the selected sensor element group, is disposed, the ultrasonic probe 10 of the radial scan type which can be connected to the ultrasonic observation apparatus 11 for the conventional ultrasonic probe of the convex scan type, and the ultrasonic diagnosing system 2 using the ultrasonic probe 10 are provided at a low cost.

Further, since the MPa 17 is provided in the first connector 14, it is relatively easy to manufacture the ultrasonic probe, which is connectable to the ultrasonic observation apparatus 11 of the convex scan type, by utilizing the structure of the conventional ultrasonic probe of the radial scan type.

Figure 6:
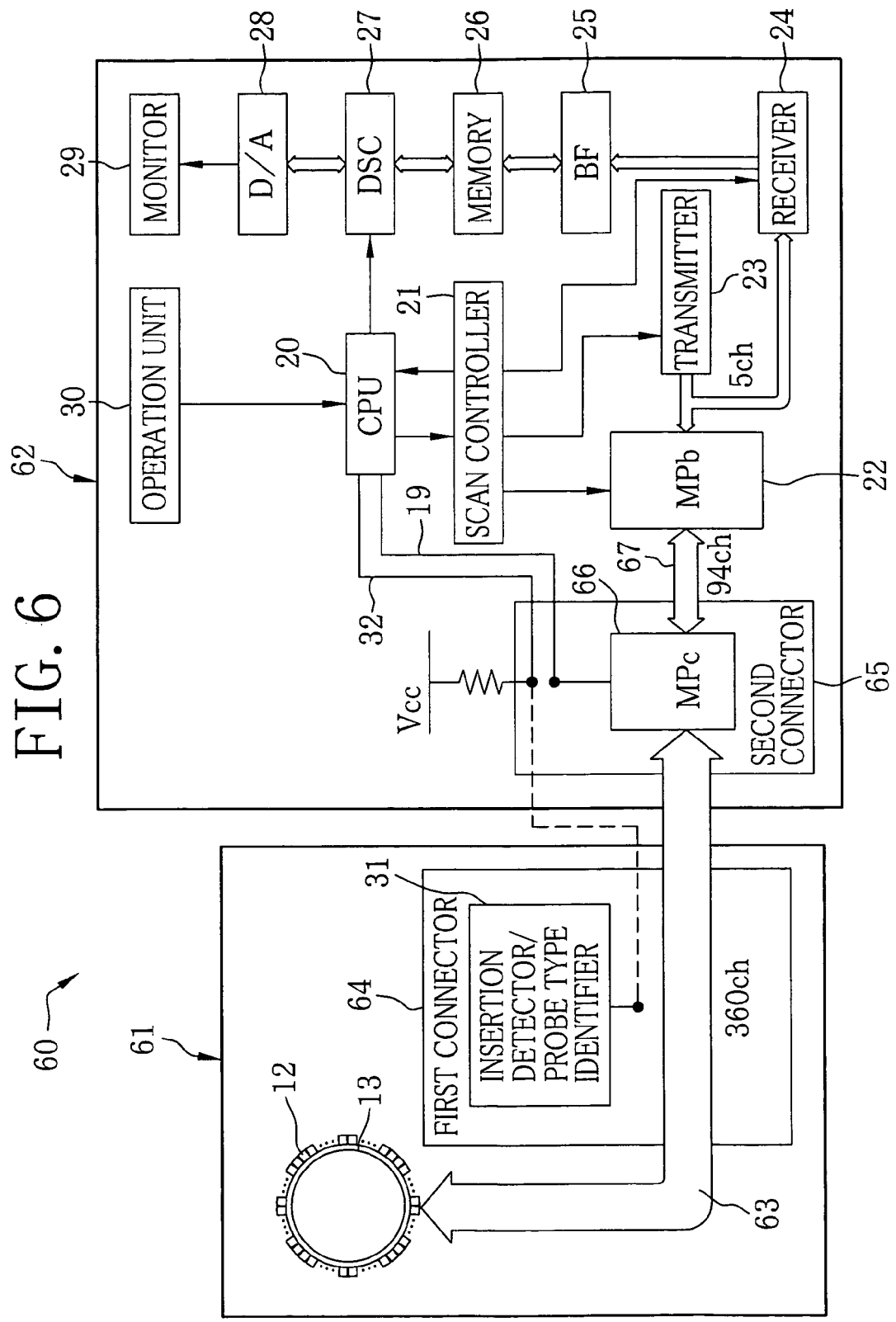
FIG. 6 is a schematic view showing a second embodiment of the ultrasonic diagnosing system.

In FIG. 6, an ultrasonic diagnosing system 60 is constructed of an ultrasonic probe 61 of the radial scan type and an ultrasonic observation apparatus 62. The ultrasonic probe 61 has the same configuration as the ultrasonic probe 10 in FIG. 1 except that the ultrasonic probe 61 does not have the MPa 17 so that 360 first signal lines 63 from the 360 ultrasonic transducers 12 are directly connected to a first connector 64.

A second connector 65 of the ultrasonic observation apparatus 62 is provided with a multiplexer (MPc) 66 which has the same configuration as the MPa 17 in FIG. 3. As with the MPa 17, the MPc 66 selectively switches the 94 first signal lines 63 of the first signal lines 63 connected through the first connector 64, and respectively connects to 94 second signal lines 67 according to the selected sensor element group among the sensor element groups 40a-40d.

The first connector 64 is formed with 360 pins which respectively correspond to 360 channels, for instance. To be compatible with both the 360 channels and 94 channels, the second connector 65 is formed with 360 pins holes, for instance. When the ultrasonic probe of the convex scan type with the 94 channels is inserted into the second connector 65, 94 pins are inserted into the pin holes which correspond to the first sensor element group 40a.

Upon receiving the insertion detection signal and the identification code from the insertion detector/probe type identifier 31, and identifying that the ultrasonic probe of the convex scan type with the 94 channels is connected, the CPU 20 controls the MPc 66 to fix the sensor element group selection signal to "00" to constantly select the first sensor element group 40a, and also controls the action of MPb 22 through the scan controller 21 (a first mode). When the CPU 20 identifies that the ultrasonic probe 10 of the radial scan type with the 360 channels is connected, the CPU 20 transmits the sensor element group selection signal to the MPc 66 through the control line 19 and also controls the action of the MPb 22 through the scan controller 21 (a second mode). Further, other configuration and the operation of the ultrasonic diagnosing system 60 are similar to the ultrasonic diagnosing system 2 shown in FIG. 1, so that the same numeral is assigned to the similar component, and the descriptions and illustrations are omitted.

As shown above in the second embodiment, since the MPc 66, which divides the 360 ultrasonic transducers 12 into four sensor element groups 40a-40d and selectively switches and connects 94 first signal lines 63 out of 360 first signal lines 63 to the second signal lines 67 according to the first to fourth sensor element groups 40a-40d, is disposed in the ultrasonic observation apparatus 62, the ultrasonic observation apparatus 62 of the convex scan type, to which the ultrasonic probe 61 of the radial scan type can also be applicable, and the ultrasonic diagnosing system 60 using the ultrasonic observation apparatus 62 are provided at low cost.

Further, since the MPc 66 is provided in the second connector 65, the ultrasonic observation apparatus, which is capable of connecting the ultrasonic probe of the radial scan type, can be manufactured with relative ease by modifying the conventional ultrasonic observation apparatus of the convex scan type.

Figure 7:
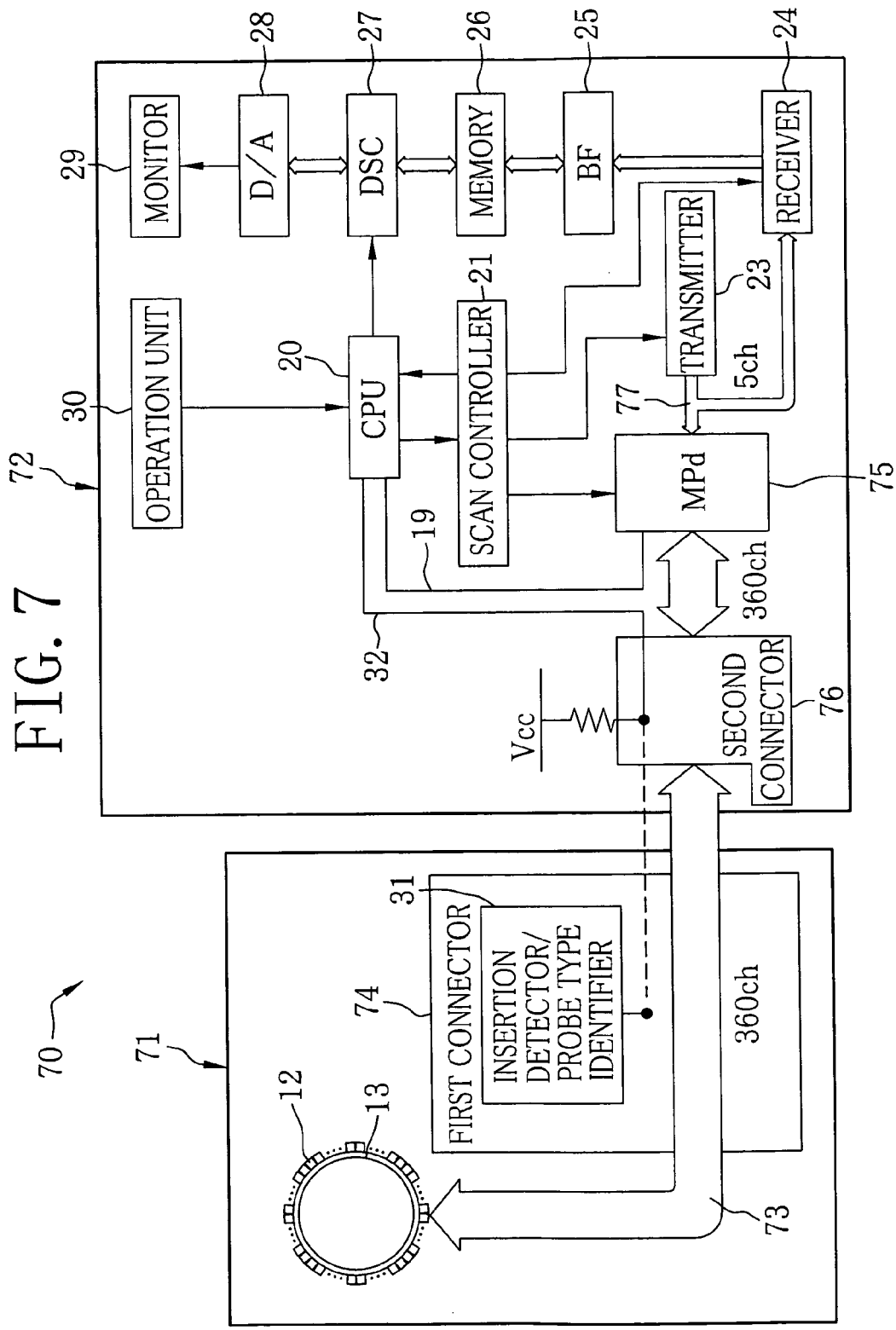
FIG. 7 is a schematic view showing a third embodiment of the ultrasonic diagnosing system.

In FIG. 7, an ultrasonic diagnosing system 70 is constructed of an ultrasonic probe 71 of the radial scan type and an ultrasonic observation apparatus 72. The ultrasonic probe 71 has the similar configuration as the ultrasonic probe 61 in FIG. 6, and 360 first signal lines 73 from the 360 ultrasonic transducers 12 are directly connected to a first connector 74.

A multiplexer (MPd) 75 is disposed in the ultrasonic observation apparatus 72. The MPd 75 selectively switches five first signal lines 73 connected through the first and second connectors 74 and 76 according to the first to fourth sensor element groups 40a-40d and connects the five first signal lines 73 to the transmitter 23 and the receiver 24 through five second signal lines 77.

Figure 8:
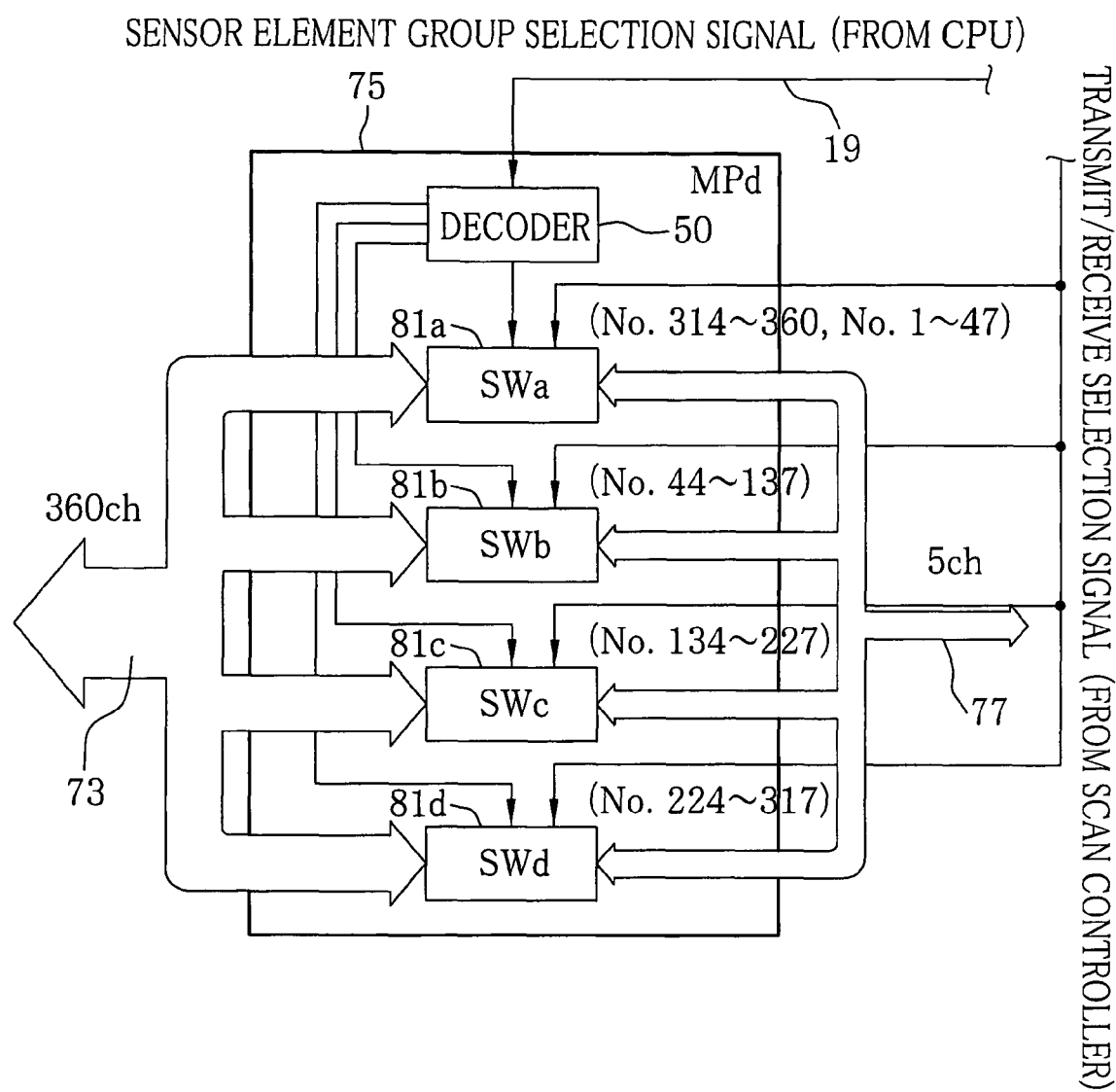
FIG. 8 is a schematic view showing a multiplexer.

As shown in FIG. 8, the MPd 75 is constructed of a decoder 80, which receives and decodes the sensor element group selection signal of two-bit sent from the CPU 20 through the control line 19, and first to fourth switches (SWa-SWd) 81a-81d.

The SWa-SWd 81a-81d selectively switch the first to fourth sensor element groups 40a-40d according to the sensor element group selection signal decoded in the decoder 80, and simultaneously drive the five ultrasonic transducers 12 as one block in the selected sensor element group under the control of the scan controller 21. Further, the MPd 75 selectively switches the ultrasonic transducer 12, which transmits and receives the drive signal and the echo signal, by shifting at least one ultrasonic transducer 12 (see FIG. 2) to be driven in the clockwise direction every time the drive signal and the echo signal are transmitted and received. That is, the MPd 75 integrates the functions of the MPa 17 and MPb 22.

The MPd 75 is constituted of a programmable logic circuit, which is capable of reprogramming an arbitrary program, such as FPGA (Field Programmable Gate Array) and the like. The CPU 20 detects the number of channels being used in the ultrasonic probe according to the identification code from the insertion detector/probe type identifier 31, and reprograms the logic circuit of the MPd 75 based on the detected results.

Similar to the second embodiment, for instance, 360 pins corresponding to 360 channels are formed in the first connector 74. The second connector 74 has 360 pin holes, for instance, to be compatible with 360 channels and 94 channels. When the ultrasonic probe of the convex scan type with 94 channels is inserted, 94 pins are inserted in the pin holes which correspond to the first sensor element group 40a.

Upon receiving the insertion detection signal and the identification code from the insertion detector/probe type identifier 31, and identifying that the ultrasonic probe of the convex scan type with the 94 channels is connected, the CPU 20, in the same manner as the second embodiment, controls the MPd 75 to fix the sensor element group selection signal to "00" to constantly select the first sensor element group 40a, and also controls the action of MPd 75 through the scan controller 21 (a first mode). When the CPU 20 identifies that the ultrasonic probe 10 of the radial scan type with the 360 channels is connected, the CPU 20 transmits the sensor element group selection signal to the MPd 75 through the control line 19 and also controls the action of the MPd 75 through the scan controller 21 (a second mode). Further, other configuration and the operation of the ultrasonic diagnosing system 70 are similar to the ultrasonic diagnosing system 2 shown in FIG. 1, so that the same numeral is assigned to the similar component, and the descriptions and illustrations are omitted.

As shown above in the third embodiment, since the MPd 75, which divides the 360 ultrasonic transducers 12 into four sensor element groups 40a-40d and selectively switches and connects five of 360 first signal lines 73 to the transmitter 23 and the receiver 24 through the five second signal lines 77 according to the first to fourth sensor element groups 40a-40d, is disposed in the ultrasonic observation apparatus 72, the ultrasonic observation apparatus 72, to which the ultrasonic probes of the convex scan type and the radial scan type are applicable, and the ultrasonic diagnosing system 70 using the ultrasonic observation apparatus 72 are provided at low cost.

Since the MPd 75 is constituted of a programmable logic circuit, which is capable of reprogramming an arbitrary program, such as FPGA (Field Programmable Gate Array) and the like, the ultrasonic probe of the convex scan type with the number of channels other than 94 can also be connected.

Further, the number of ultrasonic transducers 12, the number of ultrasonic transducers 12 included in each of the first to fourth sensor element groups 40a-40d, the number of the drive signals transmitted from the transmitter 23 and the number of the echo signals received by the receiver 24 are not limited in those described in the above embodiments. Each number can be properly changed according to a specification of the ultrasonic diagnosing system.

In the above first embodiment, the MPb 22 is disposed between the second connector 15, and the transmitter 23 and the receiver 24. In the above second embodiment, the MPb 22 is disposed between the second connector 65, and the transmitter 23 and the receiver 24. However, it is also possible to dispose the MPb 22 between the receiver 24 and the BF 25.

In the second and third embodiments described above, the second connectors 65 and 76, which are compatible with both 360 channels and 94 channels, are respectively disposed in the ultrasonic observation apparatuses 62 and 72. However, it is also possible to provide separate connectors for 360 channels and 94 channels.

In the above embodiment, the ultrasonic probe, which has the ultrasonic transducers on the outer periphery in one line, is described as an example. However, the present invention can be applied to the ultrasonic probe which has 360 ultrasonic transducers disposed on the outer periphery in plural lines. In that case, the ultrasonic transducers are divided into four sensor element groups along an axial direction of the sheath as in the same manner as the above embodiments.

In the above embodiment, only ultrasonic transducers are provided in the ultrasonic probe. However, it is also possible to integrally provide an endoscope in the ultrasonic probe.

Although the present invention has been described with respect to the preferred embodiment, the present invention is not to be limited to the above embodiment but, on the contrary, various modifications will be possible to those skilled in the art without departing from the scope of claims appended hereto.

What is claimed is:

1. An ultrasonic probe of a radial scan type mountable on an ultrasonic observation apparatus which inputs and outputs M numbers of signals in parallel, comprising:
   N(N>M) numbers of ultrasonic transducers disposed on an outer periphery of a tip of said probe, said N numbers of ultrasonic transducers being grouped into plural sensor element groups which are activated in sequence, each of said sensor element groups having M numbers of said ultrasonic transducers;
   N numbers of first signal lines respectively connected to said N numbers of ultrasonic transducers, a first signal line transmitting a drive signal for driving said ultrasonic transducers to receive an echo signal from within a living organism;
   M numbers of second signal lines connected to ultrasonic observation apparatus; and
   a multiplexer disposed between said first signal lines and said second signal lines, said multiplexer selectively switching M numbers of said first signal lines for respectively connecting to said second signal lines according to a sensor element group to be activated; and
   wherein there are four of said sensor element groups, and plural ultrasonic transducers disposed at a boundary between two adjacent sensor element groups are contained both in said two adjacent sensor element groups.

2. An ultrasonic probe of a radial scan type according to claim 1, wherein said N numbers of ultrasonic transducers are disposed throughout said outer periphery at a predetermined pitch.

3. An ultrasonic probe of a radial scan type according to claim 1, wherein said ultrasonic transducer is disposed in an endoscope.

4. The system of claim 1, wherein the boundary multiplexer respectively selecting sensor element groups sequentially, one multiplexer selection followed by another selection.

5. An ultrasonic diagnosing system comprising an ultrasonic probe of a radial scan type and an ultrasonic observation apparatus on which said ultrasonic probe of said radial scan type is mounted through a connector section thereof, said ultrasonic observation apparatus inputting and outputting M numbers of signals in parallel through said connector section, said ultrasonic diagnosing system including:
   A. said ultrasonic probe of said radial scan type including:
      N (N>M) numbers of ultrasonic transducers disposed on an outer periphery of a tip of said probe, said N numbers of ultrasonic transducers being grouped into plural sensor element groups, which are activated in sequence, each of said sensor element groups having M numbers of said ultrasonic transducers;
      N numbers of first signal lines respectively connected to said N numbers of said ultrasonic transducers, a first signal line transmitting a drive signal for driving said ultrasonic transducer to receive an echo signal from within a living organism;
      M numbers of second signal lines connected to said ultrasonic observation apparatus through said connector section; and
      a multiplexer disposed between said first signal lines and said second signal lines, said multiplexer selectively switching M numbers of said first signal lines for connecting to said second signal lines according to a sensor element group to be activated;
   B. said ultrasonic observation apparatus including:
      a scan controller which outputs a control signal to said multiplexer incorporated in said ultrasonic probe of said radial scan type for a switching operation; and
   wherein there are four of said sensor element group, and plural transducers disposed at a boundary between two adjacent sensor element groups are contained both in said two adjacent sensor element groups.

6. An ultrasonic diagnosing system according to claim 5, wherein said N numbers of ultrasonic transducers are disposed throughout said outer periphery at a predetermined pitch.

7. An ultrasonic diagnosing system according to claim 5, further including a type identifier for identifying a type of said ultrasonic probe mounted on said connector section;
   wherein according to said type identification of said type identifier, said scan controller selecting a first mode for said ultrasonic probe of said radial scan type and a second mode for an ultrasonic probe of a convex scan type which has M numbers of ultrasonic transducers disposed on an outer periphery of a tip of said probe, said scan controller outputs said control signal in said first mode, and said scan controller does not output said control signal in said second mode.

8. An ultrasonic diagnostic system according to claim 5, wherein said ultrasonic transducer is disposed in an endoscope.

9. An ultrasonic observation apparatus, on which an ultrasonic probe having ultrasonic transducers is mountable, comprising:
- a connector section which is capable of connecting N numbers of first signal lines, said first signal lines respectively connected to said ultrasonic transducers, said transducers being grouped into plural sensor element groups;
- a first multiplexer for selectively switching M numbers of said first signal lines to connect to M numbers of second signal lines;
- a second multiplexer for selectively switching L(N>M>L) numbers of said second signal lines to connect to a transmitter for transmitting a drive signal, or a receiver for receiving an echo signal;
- a scan controller for controlling switching operations of said first and second multiplexers; and
- wherein there are four of said sensor element groups, and plural ultrasonic transducers disposed at a boundary between two adjacent sensor element groups are contained both in said two adjacent sensor element groups.

10. An ultrasonic observation apparatus according to claim 9, further including a type identifier for identifying a type of an ultrasonic probe mounted on said connector section;
- wherein according to said type identification of said type identifier, said scan controller selects a first mode for an ultrasonic probe of a radial scan type, which has N numbers of ultrasonic transducers on an outer periphery of a tip of said probe, and a second mode for an ultrasonic probe of a convex scan type which has M numbers of ultrasonic transducers on an outer periphery of a tip of said probe, said first multiplexer performing said switching operation in said first mode, and said first multiplexer not performing said switching operation in said second mode.

11. The system of claim 9, wherein the first multiplexer and second multiplexer are different types of multiplexers, wherein the multiplexers select signal lines in sequence, selection of L lines followed by selection of M lines.

12. An ultrasonic diagnosing system including an ultrasonic probe of a radial scan type which has N numbers of ultrasonic transducers on an outer periphery of a tip of said probe, said transducers being grouped into plural sensor element groups, and an ultrasonic observation apparatus on which said ultrasonic probe of said radial scan type is mountable, L numbers of said ultrasonic transducers being simultaneously driven as one block, at least one of said ultrasonic transducers to be driven being shifted every time a drive signal for driving said ultrasonic transducer being transmitted or an echo signal from within a living organism being received, said ultrasonic observation apparatus generating an ultrasonic image from said echo signal sequentially received on said block basis, said ultrasonic observation apparatus including:
- a connector section which is capable of connecting N numbers of first signal lines which are respectively connected to said ultrasonic transducers;
- a first multiplexer for selectively switching M (N>M>L) numbers of said first signal lines to connect to M second signal lines;
- a second multiplexer for selectively switching L numbers of said second signal lines to connect to a transmitter for transmitting said drive signal, or a receiver for receiving said echo signal; and
- a scan controller for controlling switching operations of said first and second multiplexers; and
- wherein there are four of said sensor element groups, and plural ultrasonic transducers disposed at a boundary between two adjacent sensor element groups are contained both in said two adjacent sensor element groups.

13. An ultrasonic diagnosing system according to claim 12, wherein said N numbers of ultrasonic transducers are disposed throughout said outer periphery at a predetermined pitch.

14. An ultrasonic diagnosing system according to claim 12, further including a type identifier for identifying a type of an ultrasonic probe mounted thereon through said connector section;
- wherein according to said type identification of said type identifier, said scan controller selects a first mode for said ultrasonic probe of said radial scan type, and a second mode for an ultrasonic probe of a convex scan type, which has M numbers of ultrasonic transducers on an outer periphery of a tip of said probe, said first multiplexer performing said switching operation in said first mode, said first multiplexer not performing said switching operation in said second mode.

15. An ultrasonic diagnosing system according to claim 12, wherein said ultrasonic transducer is disposed in an endoscope.

16. An ultrasonic observation apparatus which is capable of mounting an ultrasonic probe of a radial scan type which has N numbers of ultrasonic transducers and an ultrasonic probe of a convex scan type which has M numbers of ultrasonic transducers on an outer periphery of a tip of said probe, wherein said N numbers of ultrasonic transducers are grouped into plural sensor element groups, and wherein L (N>M>L) numbers of said ultrasonic transducers being simultaneously driven as one block, at least one of said ultrasonic transducers to be driven being shifted every time a drive signal for driving said ultrasonic transducer being transmitted or an echo signal from within a living organism being received, an ultrasonic image being generated from said echo signal sequentially received on said block basis, said ultrasonic observation apparatus including:
- a connector section on which said ultrasonic probe of said radial scan type or said ultrasonic probe of said convex scan type is mounted, N numbers of first signal lines, which are respectively connected to said ultrasonic transducers, being connectable to said connector section;
- a first multiplexer for selectively switching M numbers of said first signal lines to connect to M numbers of second signal lines;
- a second multiplexer for selectively switching L numbers of said second signal lines to connect to a transmitter for transmitting said drive signal, or a receiver for receiving said echo signal;
- a scan controller for controlling switching operations of said first and second multiplexers, said scan controller selecting a first mode for said ultrasonic probe of said radial scan type, and a second mode for said ultrasonic probe of said convex scan type, said first multiplexer performing said switching operation in said first mode, said switching operation not being performed in said second mode; and
- wherein there are four of said sensor element groups, and plural ultrasonic transducers disposed at a boundary between two adjacent sensor element groups are contained both in said two adjacent sensor element groups.

17. An ultrasonic observation apparatus according to claim 16, further including:

a type identifier for identifying a type of an ultrasonic probe mounted on said connector section;

wherein according to said type identification of said type identifier, said scan controller selects one of said first mode and said second mode.

18. An ultrasonic diagnosing system comprising an ultrasonic probe of a radial scan type and an ultrasonic observation apparatus on which said ultrasonic probe of said radial scan type is mounted through a connector section thereof, said ultrasonic observation apparatus inputting and outputting M numbers of signals in parallel through said connector section, said ultrasonic diagnosing system including:

A. said ultrasonic probe of said radial scan type including:
N (N>M) numbers of ultrasonic transducers disposed on an outer periphery of a tip of said probe, said N numbers of ultrasonic transducers being grouped into plural sensor element groups, which are activated in sequence, each of said sensor element groups having M numbers of said ultrasonic transducers;
N numbers of first signal lines respectively connected to said N numbers of ultrasonic transducers for transmitting drive signals for driving said ultrasonic transducers and echo signals from within a living organism;
M numbers of second signal lines connected to said ultrasonic observation apparatus through said connector section; and
a first multiplexer disposed between said first signal lines and said second signal lines, said first multiplexer selectively switching M numbers of said first signal lines for connecting to said second signal lines according to said sensor element group to be activated;

B. said ultrasonic observation apparatus including:
a second multiplexer which selectively switches L numbers of said second signal lines to connect to a transmitter for transmitting said drive signal or a receiver for receiving said echo signal;
a scan controller for performing said switching operations of said first and second multiplexers, and
wherein there are four of said sensor element groups, and plural ultrasonic transducers disposed at a boundary between two adjacent sensor element groups are contained both in said two adjacent sensor element groups.

19. An ultrasonic diagnosing system according to claim 18, wherein said connector section includes a first connector and a second connector which are mutually connected, said first connector is disposed in said ultrasonic probe of said radial scan type, and said second connector is disposed in said ultrasonic observation apparatus.

20. An ultrasonic diagnosing system according to claim 19, wherein said first multiplexer is disposed in said first connector, and said second multiplexer is disposed in said second connector.

21. An ultrasonic diagnosing system according to claim 19, wherein said first multiplexer is disposed in said first connector, and said second multiplexer is disposed between said transmitter and said receiver, and said second connector.

22. An ultrasonic diagnosing system according to claim 18, wherein said multiplexer is a programmable logic circuit in which an arbitrary logic is reprogrammable.

23. An ultrasonic diagnosing system according to claim 18, wherein said N numbers of ultrasonic transducers are disposed throughout said outer periphery at a predetermined pitch.

24. An ultrasonic diagnosing system according to any one of claim 18, 19, 20, 21 or 22, further including a type identifier for identifying a type of an ultrasonic probe mounted through said connector section;

wherein according to said type identification of said type identifier, said scan controller selects a first mode for said ultrasonic probe of said radial scan type, and a second mode for an ultrasonic probe of a convex scan type which has M numbers of ultrasonic transducers on an outer periphery of a tip of said probe, said first multiplexer performs said switching operation in said first mode, and said switching operation not being performed in said second mode.

25. An ultrasonic diagnosing system according to claim 18, wherein said ultrasonic transducer is disposed in an endoscope.

26. An ultrasonic diagnosing system comprising an ultrasonic probe of a radial scan type and an ultrasonic observation apparatus to which said ultrasonic probe of said radial scan type is connected through a connector section thereof, said ultrasonic diagnosing system including:

A. said ultrasonic probe of said radial scan type including:
N (N>M) numbers of ultrasonic transducers disposed on an outer periphery of a tip of said probe, said N numbers of ultrasonic transducers being grouped into plural sensor element groups, each of said sensor element group having M numbers of ultrasonic transducers;

B. said ultrasonic observation apparatus including:
a transmitter for transmitting driving signal for driving a predetermined number of said ultrasonic transducers;
a receiver for receiving an echo signal reflected from within a living organism;
a display for displaying an ultrasonic image generated from said echo signal;

C. a multiplexer disposed in whether said ultrasonic probe of said radial scan type or said ultrasonic observation apparatus, said multiplexer sequentially selecting one of said sensor element groups to be activated by a switching operation; and
wherein there are four of said sensor element groups, and plural transducers disposed at a boundary between two adjacent sensor element groups are contained both in said two adjacent sensor element groups.

27. An ultrasonic diagnosing system according to claim 26, wherein said connector section includes a first connector and a second connector which are mutually connected, said first connector is disposed in said ultrasonic probe of said radial scan type, and said second connector is disposed in said ultrasonic observation apparatus.

28. An ultrasonic diagnosing system according to claim 27, wherein said multiplexer is disposed in said first connector or in said second connector.

29. An ultrasonic diagnosing system according to claim 27, wherein said ultrasonic transducer is disposed in an endoscope.

30. An ultrasonic diagnosing system according to claim 26, wherein said multiplexer is a programmable logic circuit in which an arbitrary logic is reprogrammable.

31. An ultrasonic diagnosing system according to claim 26, wherein said N numbers of ultrasonic transducers are disposed throughout said outer periphery at a predetermined pitch.

32. An ultrasonic diagnosing system according to any one of claim 26, 27, 28 or 30, said ultrasonic observation apparatus further including a type identifier for identifying a type of an ultrasonic probe mounted through said connector section;

wherein according to said type identification of said type identifier, said scan controller selects a first mode for said ultrasonic probe of said radial scan type, and a second mode for an ultrasonic probe of a convex scan type which has M numbers of ultrasonic transducers on an outer periphery of a tip of said probe, said multiplexer performs a switching operation in said first mode, and does not perform said switching operation in said second mode.

* * * * *